US011263501B2

(12) United States Patent
Liu et al.

(10) Patent No.: US 11,263,501 B2
(45) Date of Patent: Mar. 1, 2022

(54) GENERATING REPORTS OF THREE DIMENSIONAL IMAGES

(71) Applicant: Siemens Healthcare GmbH, Erlangen (DE)

(72) Inventors: Ning Liu, Beijing (CN); Ying Chi, Beijing (CN)

(73) Assignee: Siemens Healthcare GmbH, Erlangen (DE)

( * ) Notice: Subject to any disclaimer, the term of this patent is extended or adjusted under 35 U.S.C. 154(b) by 18 days.

(21) Appl. No.: 16/864,414

(22) Filed: May 1, 2020

(65) Prior Publication Data

US 2020/0349402 A1 Nov. 5, 2020

(30) Foreign Application Priority Data

May 2, 2019 (EP) .................................... 19172268

(51) Int. Cl.
*G06K 9/72* (2006.01)
*G06K 9/00* (2006.01)
*G06K 9/62* (2006.01)
*G16H 15/00* (2018.01)

(52) U.S. Cl.
CPC ......... *G06K 9/726* (2013.01); *G06K 9/00201* (2013.01); *G06K 9/628* (2013.01); *G06K 9/6256* (2013.01); *G16H 15/00* (2018.01)

(58) Field of Classification Search
CPC .. G06K 9/726; G06K 9/00201; G06K 9/6256; G06K 9/628; G16H 15/00
See application file for complete search history.

(56) References Cited

U.S. PATENT DOCUMENTS

2010/0131873 A1* 5/2010 Mejia ..................... G16H 30/40
715/764
2020/0219609 A1* 7/2020 Harte ..................... G16H 15/00

FOREIGN PATENT DOCUMENTS

WO 2018094438 A1 5/2018
WO WO-2019030410 A1 * 2/2019 ............... G06N 3/04

OTHER PUBLICATIONS

Jing, Baoyu et al: "On the Automatic Generation of Medical Imaging Reports", arxiv.org; Cornell University Library; 201 Olin Library Cornell University Ithaca, NY 14853; Jul. 20, 2018; pp. 1-10; XP081106033, Retrieved from the Internet: URL:https://arxiv.org/pdf/1711.08195.pdf.

(Continued)

*Primary Examiner* — Casey L Kretzer
(74) *Attorney, Agent, or Firm* — Schiff Hardin LLP

(57) ABSTRACT

Various techniques are provided for generating reports of three dimensional (3D) images. The techniques include identifying a plurality of volume features in a 3D image using a first machine learning (ML) module trained with annotated 3D images, and identifying a plurality of semantic representations associated with the 3D image using a second ML module trained with the annotated 3D images and reports associated with the annotated 3D images. The techniques further include generating a report of the 3D image based on the volume features and the semantic representations using a third ML module trained with the reports and outputs generated by the first ML module and the second ML module using the annotated 3D images and the reports.

18 Claims, 6 Drawing Sheets

(56) References Cited

OTHER PUBLICATIONS

Shin, Hoo-Chang et al: "Learning to Read Chest X-Rays: Recurrent Neural Cascade Model for Automated Image Annotation", 2016 IEEE Conference on Computer Vision and Pattern Recognition (CVPR); Jun. 26, 2016; pp. 2497-2506, XP055544272.

Bernardi, Raffaella et al: "Automatic Description Generation from Images: A Survey of Models, Datasets, and Evaluation Measures", arxiv.org; Cornell University Library, 201 Olin Library Cornell University Ithaca, NY 14853; Jan. 15, 2016; XP080679061; Retrieved from the Internet: URL:https://arxiv.org/pdf/1601.03896v1.pdf.

European Search Report dated Nov. 13, 2019, for Application 19172268.5.

* cited by examiner

GENERATING REPORTS OF THREE DIMENSIONAL IMAGES

CROSS-REFERENCE TO RELATED APPLICATIONS

The present application claims the benefit of the filing date of European patent application no. EP 19172268.5, filed on May 2, 2019, the contents of which are incorporated herein by reference in their entirety.

TECHNICAL FIELD

The present disclosure relates to image processing technologies. More particularly, the present disclosure relates to a method and apparatus of generating reports of three dimensional (3D) images.

BACKGROUND

Three dimensional (3D) imaging techniques, such as ultrasound, Computed Tomography (CT), Magnetic Resonance Imaging (MRI), positron emission tomography (PET), and the like, are capable of producing three-dimensional representations of a scanned structure, and are widely used in many areas such as medical diagnosis, mechanical fault detection, reverse engineering, etc. 3D images are read by field experts who then compose analysis reports on the findings and impressions.

SUMMARY

This section provides a general summary of the disclosure, and is not a comprehensive disclosure of its full scope or all of its features.

Various examples provide a method of generating reports of 3D images, including:

identifying a plurality of volume features in a 3D image using a first machine learning, ML, module trained with annotated 3D images;

identifying a plurality of semantic representations associated with the 3D image using a second ML module trained with the annotated 3D images and reports associated with the annotated 3D images; and generating a report of the 3D image based on the volume features and the semantic representations using a third ML module trained with the reports and outputs generated by the first ML module and the second ML module using the annotated 3D images and the reports.

According to various examples, not only volume features but also semantic representations are obtained from a 3D image, and both are used in generating an analysis report of the 3D image, which can ensure most of important features can be covered by the generated report.

In some examples, the procedure of identifying a plurality of semantic representations associated with the 3D image using a second ML module may include:

identifying semantic representations of attributes associated with volume structures in the 3D image using a multi-label classification module of the second ML module, the multi-label classification module is trained using the annotated 3D images and semantic representations obtained from the reports associated with the annotated 3D images.

As such, more information can be provided to guide subsequent generation of the report than just a list of names of structures and abnormalities, thus the report can provide extra information such as descriptive statements, negation statements or uncertainty statements which may be more useful.

According to some examples, the procedure of generating the report of the 3D image may include:

selecting a semantic element from a pre-defined element set at each time step using the third ML module, the volume features, the semantic representations and a semantic element selected in a previous time step; and adding the selected semantic element into the report.

By generating a semantic element at each time step based on already generated report, contents of the generated report can be well arranged with strong ties between elements.

According to some examples, the pre-defined element set may be a pre-defined vocabulary, and the procedure of selecting the semantic element from the pre-defined element set may include:

calculating a conditional probability value of each semantic element in the pre-defined vocabulary given semantic elements selected in previous time steps and the semantic representations using the third ML module; and selecting the semantic element according to the conditional probability value of each semantic element in the vocabulary.

By taking the probabilities of the semantic elements into consideration and selecting a semantic element according to the conditional probability value, the selection process can be more efficient and accurate.

According to some examples, the method may also include:

determining parameters of the first ML module using annotations of volume structures in the annotated 3D images;

determining parameters of the third ML module using the annotated 3D images, the reports, and results generated from processing the annotated 3D images by the first ML module and the second ML module; and adjusting the parameters of the first ML module using feedback generated by the third ML module while determining the parameters of the third ML module.

As such, through providing feedback between ML modules, the overall performance of the report generating method can be improved.

According to some examples, the method may also include:

determining parameters of one of the first ML module and the second ML module by training the one of the first ML module and the second ML module using annotations of volume structures in the annotated 3D images; and initializing the other of the first ML module and the second ML module using the parameters.

By training one of the first ML module and the second ML module and initializing the other of the first ML module and the second ML module using trained parameters, resources and time needed for the training can be reduced.

According to some examples, the method may also include:

obtaining history examination records generated by an image processing workstation, the history examination records comprising one or more of: history 3D images, marks on the history 3D images generated in the image processing workstation, and history analysis reports associated with the history 3D images;

providing the history 3D images as the annotated 3D images, providing the marks as annotations of the annotated 3D images, and providing the history analysis reports as the reports associated with the annotated 3D images.

By obtaining the annotated 3D images and associated reports from history examination records provided by an image processing workstation, the ML modules can be trained without requiring additional annotation work.

Various examples provide apparatus of generating reports of 3D images, including:

an image feature identifying module, configured to identify a plurality of volume features in a 3D image using a first machine learning, ML, module trained with annotated 3D images;

a semantic attribute predicting module, configured to identify a plurality of semantic representations associated with the 3D image using a second ML module trained with the annotated 3D images and reports associated with the annotated 3D images; and a report generating module, configured to generate a report of the 3D image based on the volume features and the semantic representations using a third ML module trained with the reports and outputs generated by the first ML module and the second ML module using the annotated 3D images and the reports.

According to various examples, the apparatus obtains not only volume features but also semantic representations from a 3D image, and uses both in generating an analysis report of the 3D image, thus ensuring the most important features can be covered by the generated report.

According to some examples, the semantic attribute predicting module may:

identify semantic representations of attributes associated with volume structures in 3D image using a multi-label classification module of the second ML module, the multi-label classification module is trained using the annotated 3D images and semantic representations obtained from the reports associated with the annotated 3D images.

As such, the semantic attribute predicting module can provide more information to guide subsequent generation of the report than just a list of names of structures and abnormalities, thus the report can provide extra information such as descriptive statements, negation statements, or uncertainty statements, which may be more useful.

According to some examples, the report generating module may:

select a semantic element from a pre-defined element set at each time step using the third ML module, the volume features, the semantic representations, and a semantic element selected in a previous time step; and add the selected semantic element into the report.

By generating a semantic element at each time step based on already generated report, the apparatus can generate reports having well-arranged contents with strong ties between elements.

According to some examples, the pre-defined element set may be a pre-defined vocabulary, and the report generating module may:

calculate a conditional probability value of each semantic element in the vocabulary given semantic elements selected in previous time steps and the semantic representations using the third ML module;

select the semantic element according to the conditional probability value of each semantic element in the vocabulary.

By taking the probabilities of the semantic representations into consideration and selecting a semantic element according to the conditional probability value, the selection process can be more efficient and accurate.

According to some examples, the apparatus may also include:

a training module, configured to:

determine parameters of the first ML module using annotations of volume structures in the annotated 3D images;

determine parameters of the third ML module using the annotated 3D images, the reports, and results generated from processing the annotated 3D images by the first ML module and the second ML module;

adjust the parameters of the first ML module using feedback generated by the third ML module while determining the parameters of the third ML module.

As such, through the backward propagation between ML modules, the overall performance of the report generating apparatus can be improved.

According to some examples, the apparatus may also include:

a training module, configured to:

determine parameters of one of the first ML module and the second ML module by training the one of the first ML module and the second ML module using annotations of volume structures in the annotated 3D images; and initializing the other of the first ML module and the second ML module using the parameters.

By training one of the first ML module and the second ML module and initializing the other of the first ML module and the second ML module using trained parameters, resources and time needed for the training can be reduced.

According to some examples, the apparatus may also include:

a data obtaining module, configured to:

obtain history examination records generated by an image processing workstation, the history examination records comprise: history 3D images, marks on the history 3D images generated in the image processing workstation, and history analysis reports associated with the history 3D images;

provide the history 3D images as the annotated 3D images, provide the marks as annotations of the annotated 3D images, and provide the history analysis reports as the reports associated with the annotated 3D images.

By obtaining the annotated 3D images and associated reports from history examination records provided by an image processing workstation, the ML modules can be trained without requiring additional annotation work.

Various examples also provide a computer-readable storage medium, comprising computer-readable instructions executable by a processor to carry out the method of various examples.

BRIEF DESCRIPTION OF THE DRAWINGS/FIGURES

For a better understanding of the present disclosure, reference should be made to the Detailed Description below, in conjunction with the following drawings in which like reference numerals refer to corresponding parts throughout the figures.

DETAILED DESCRIPTION

Reference will now be made in detail to examples, which are illustrated in the accompanying drawings. In the following detailed description, numerous specific details are set forth in order to provide a thorough understanding of the present disclosure. Also, the figures are illustrations of examples, in which modules or procedures shown in the figures are not necessarily essential for implementing the present disclosure. In other instances, well-known methods, procedures, components, and circuits have not been described in detail so as not to unnecessarily obscure aspects of the examples.

An analysis report of an examination image is a summary of all the findings and impressions obtained during an examination, e.g., in a medical examination, a mechanical examination, or the like. The report sentences are listed as descriptions for each part examined. A description of a normal finding may be like: a certain part is normal or no findings in a certain part. A description of an abnormal finding may be more likely in this format: some disease or abnormality or fault is at a certain part with properties such as severity, dimensions of the abnormality, shape of the abnormality, etc. An analysis report usually includes richer information than just disease keywords or fault keywords, and also may consist of negation and uncertainty statements. Suspicious findings may cause recommendations for additional or follow-up imaging studies. As such, an analysis report consists of a challenging mixture of information which is hard to produce.

Figure 1:
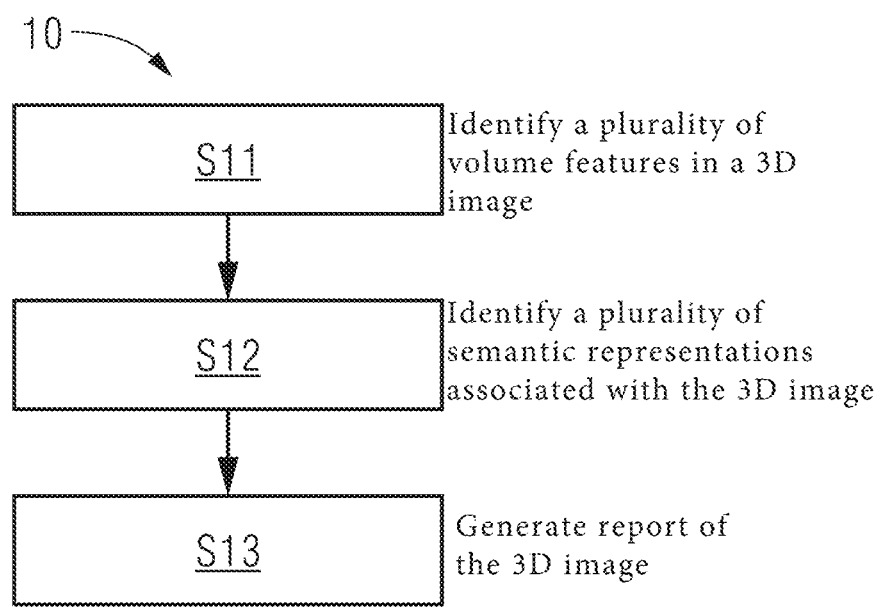
FIG. 1 is an example flowchart illustrating a method of generating reports of 3D images in accordance with various aspects of the present disclosure.

Various examples provide a method of generating reports of 3D images. The 3D images may be images for examination or inspection purposes, e.g., for medical inspection, mechanical examination, or the like. The 3D images may also be referred to as 3D inspectional images or 3D examination images herein. The 3D images may be generated by various imaging techniques, e.g., ultrasound, CT, MRI, PET, etc. As shown in FIG. 1, the method 10 may include the following procedures.

At block S11, a plurality of volume features in a 3D image may be identified using a first machine learning (ML) module trained with annotated 3D images.

A volume feature refers to information distributed within an amount of space having a certain height, length, and width. Volume features may be data representing a structure in a 3D image or in a transformed version of a 3D image. A structure refers to one or a set of objects (e.g., a mechanical structure, a body part, or the like), one or a set of features associated with an object (e.g., a region, a cavity, a fissure, a tumor, a stenosis, a calcification flake, or the like), etc., or a combination thereof. A transformed version of a 3D image may be data obtained by processing the 3D image through a transformation operation, e.g., a geometric transformation, a mathematical transformation, or the like. A geometric transformation may be such operations as image scaling, or the like. A mathematical transformation may be such operations as convolution, up-convolution, or the like. In order to handle the 3D image data within the 3D space to extract features that exist across the three spatial dimensions, the transformation operation may be a 3D version operation, e.g., 3D scaling, 3D convolution, etc.

An annotated 3D image refers to a 3D image having annotations. The annotations refer to additional information about at least one structure in a 3D image generated in a process independent of the process of generating the 3D image. The annotations may include marks made by an expert on the 3D image. In some examples, the annotations may also include category information of the 3D image, or the like.

As used herein, a mark refers to an indication made on a voxel in the 3D image, usually manually added by an expert, for identifying a structure illustrated in the 3D image. A mark may be stored as data associated with information of a voxel in the 3D image. For example, a mark may be identified using coordinate information of the voxel where the mark is made. A mark may also be associated with identification information of the structure, e.g., a mark made on a body part may be associated with identification information specifying the name of the body part, or the like. For example, a mark may be stored as data including coordinates of a voxel and a name of a structure, e.g., in a form such as {(2, 2, 5), "tumor"}, or the like. In another example, a mark may be stored in a mark list associated with a structure, e.g., in a form such as {"stenosis_1", (2, 2, 3), (4, 2, 5) . . . }, or the like. A 3D image may include a large amount of marks identifying at least one structure illustrated in the image, e.g., marks identifying a part or a region in the 3D image, marks identifying the outline of an abnormality, or the like.

The category information of a 3D image refers to information about at least one category the 3D image belongs to. A 3D image may belong to at least one category, e.g., a category corresponding to the examined part, or a category corresponding to the department that prescribed the examination, or a category corresponding to a type of abnormality to be inspected, or the like. The category information may be automatically generated by an image processing work station, or obtained from information manually inputted or selected by an expert (e.g., a directory storing the 3D image, a file name of the 3D image, etc.), or the like.

The first ML module may be trained using the annotated 3D images, i.e., using the 3D images and annotations associated with the 3D images. During training, the first ML module may take the 3D images as input and the annotations as the ground truth to train parameters of the first ML module. As such, the first ML module is able to identify volume features from an input 3D image and/or from a transformed version of the input 3D image.

At block S12, a plurality of semantic representations associated with the 3D image may be identified using a second ML module trained with the annotated 3D images and reports associated with the annotated 3D images.

A semantic representation refers to a representation of a semantic element which is descriptive of the image. The semantic element refers to a segment of text, e.g., a word, a phrase, a sentence segment, a sentence, or the like. A semantic representation may be in a form that can be processed by a computer, e.g., a string of numbers, a vector of real numbers, or the like. A semantic representation may be generated by processing a semantic element using natural language processing (NLP) techniques. For example, a semantic representation of a word may be generated using techniques such as Bag-of-Words, Term Frequency—Inverse Document Frequency (TF-IDF), or the like.

The second ML module may be trained using the annotated 3D images and associated reports, so as to be able to identify characteristics of a 3D image and find out semantic information descriptive of the characteristics.

At block S13, a report of the 3D image may be generated based on the volume features and the semantic representations using a third ML module, and the third ML module may be trained with the annotated 3D images, the reports, and the outputs generated by the first ML module and the second ML module using the annotated 3D images and the reports.

The third ML module may be trained using the annotated 3D images and the reports to learn the relationships between volume features and semantic elements (e.g., words, phrases, sentences, or the like) in the reports, the relationships between the semantic elements and relative relations between the volume features (e.g., position relations, size relations, or the like), the relationships between the semantic elements in the reports, and the like. Further, the training of the third ML module may also use outputs of the second ML module to enhance the report generation performance. Thus, the third ML module is able to generate a report based on volume features extracted by the first ML module, the semantic representations obtained by the second ML module, and the learned relationships.

According to various examples, not only volume features but also semantic representations are obtained from a 3D image, and both are used in generating an analysis report of the 3D image, which can ensure most of important features are covered by the generated report.

In various examples, the ML modules may use any or any combinations of machine learning algorithms, such as artificial neural networks (ANN), multi-layer perceptron (MLP), regression, classifiers, reinforcement learning, or the like.

Figure 2:
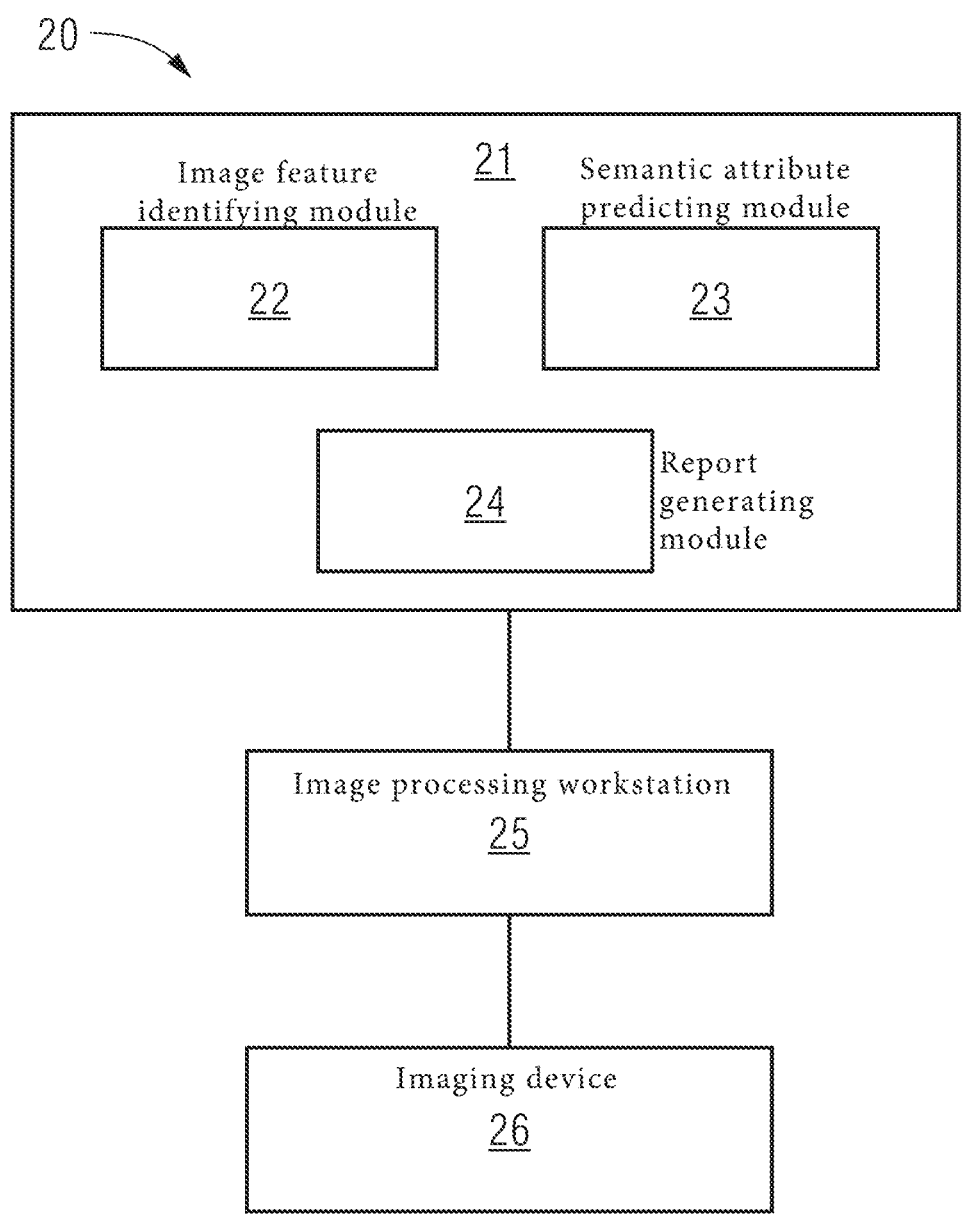
FIG. 2 is an example schematic diagram illustrating a system for processing 3D images in accordance with various aspects of the present disclosure.

The method of various examples may be implemented by an apparatus, referred to hereinafter as report generating apparatus. The report generating apparatus may be a stand-alone computing device, or may be a component of a computing device. The report generating apparatus may be employed in a system for processing 3D images, e.g., the system 20 as shown in FIG. 2. As shown in FIG. 2, the system 20 may include a report generating apparatus 21, an image processing workstation 25, and an imaging device 26. The report generating apparatus may include one or more processors, hardware components, software components, or any combination thereof.

The imaging device 26 may generate 3D images using a scanner, e.g., a CT scanner, an MRI scanner, or the like.

The image processing workstation 25 may be a device for processing, storing and communicating images, or the like. For example, in clinical scenarios, the image processing workstation 25 may be a device running a management system such as hospital information system (HIS), picture archiving and communication systems (PACS), radiology information system (RIS), or the like. The image processing workstation 25 may process and store the 3D images generated by the imaging device 25, e.g., generate category information for a 3D image, associate a 3D image with a customer identity or an examination record, associate a 3D image with an analysis report, or the like. The image processing workstation 25 may store the 3D images and associated information into a storage device, e.g., a hard drive, a remote database device, or the like. The image processing workstation 25 may provide the 3D images for the report generating apparatus 21, either directly via a wire or wireless communication link, or via a storage device. For example, the image processing workstation 25 may store a 3D image and associated information into a storage device, and the report generating apparatus 21 may obtain the 3D image from the storage device when necessary, e.g., when an analysis report for the 3D image is required to be generated.

The report generating apparatus (or report generating circuitry or a report generator) 21 may be a device capable of communicating with the image processing workstation 25, and may be implemented using any suitable number and/or type of processors, hardware components, software components, or a combination of any of these. The report generating device 21 may communicate directly or indirectly with the image processing workstation 25, e.g., via a wired or wireless communication link or network, or via another device such as a storage device, or the like. As shown in FIG. 2, the report generating apparatus 21 may include an image feature identifying module 22, a semantic attribute predicting module 23, and a report generating module 24.

The image feature identifying module 22 may identify a plurality of volume features in a 3D image using a first machine learning (ML) module trained with annotated 3D images.

The semantic attribute predicting module 23 may identify a plurality of semantic representations associated with the 3D image using a second ML module trained with the annotated 3D images and reports associated with the annotated 3D images.

The report generating module 24 may generate a report of the 3D image based on the volume features, the semantic representations using a third ML module trained with the annotated 3D images, the reports, and outputs of the first ML module and the second ML module generated based on the annotated 3D images and the reports.

In some examples, the report generating apparatus 21 may be implemented by hardware modules, e.g., dedicated logic circuits or chips, FPGA, ASIC, or the like. In other examples, the report generating apparatus 21 may be implemented by general-purpose processors. For example, the report generating apparatus 21 may include a processor and a memory storing computer-readable instructions corresponding to the modules of the report generating apparatus 21, e.g., the image feature identifying module 22, the semantic attribute predicting module 23, and the report generating module 24. The instructions are executable by the processor to implement the functions of the report generating apparatus 21.

In some examples, the system 20 may include a plurality of report generating apparatus 21, and each report generating apparatus 21 may be employed to generate reports for a specific type of 3D images. In some examples, the report generating apparatus 21 may include a plurality of sets of the ML modules, and each set of the ML modules may be trained for processing a specific type of 3D images. The type of a 3D image may refer to the part examined, the type of anomaly inspected in the examination, or the like. The type of a 3D image may be obtained from category information generated by the image processing workstation 25, a directory storing the 3D image, a file name of the 3D image, or the like. For example, when an expert performs an examination, he/she may select category information for the image generated in the workstation, e.g., the clinical department that prescribed the examination, the examined part, the abnormality to be inspected, or the like. According to the type of the 3D image, one of the plurality of report generating apparatus 21 or one of the sets of ML modules associated with the type may be activated to process the 3D image. A plurality sets of ML modules may be used to generate one or a plurality of reports for one 3D image. For example, in an integrated scan like a chest CT scan (which includes heart and lung in one scan), it can generate a heart report and a lung report, or a report including contents about the heart and contents about the lung, by using a combination of two sets of ML modules, including one set of ML modules is for heart and the other set of ML modules is for lung.

According to various examples, the report generating apparatus may generate an analysis report of a 3D image using not only volume features but also semantic representations obtained from a 3D image, thus can generate an analysis report that covers most of important features in the 3D image.

In various examples, the image feature identifying module 22 may identify volume features of an examined part (e.g., a mechanical component, a body part, or the like) and volume features of an anomaly associated with the examined part, i.e., volume features of volume structures. Identification of the anomaly is often more important. Anomalies in different cases may have different shape, size, or the like, thus it is challenging to correctly extract volume features of anomalies from the 3D image. To address the issue, in some examples, the procedure at step S11 may be performed as follows. The 3D image may be processed through a plurality of pre-determined transformation operations to generate transformed versions of the 3D image, and the volume features associated with the volume structures may be identified from the 3D image and the transformed versions using the first ML module. Since the transformation operations can deform structures in the 3D image, using the transformed versions of the image can increase the chances that volume features of the structures are identified and extracted.

Figure 3A:
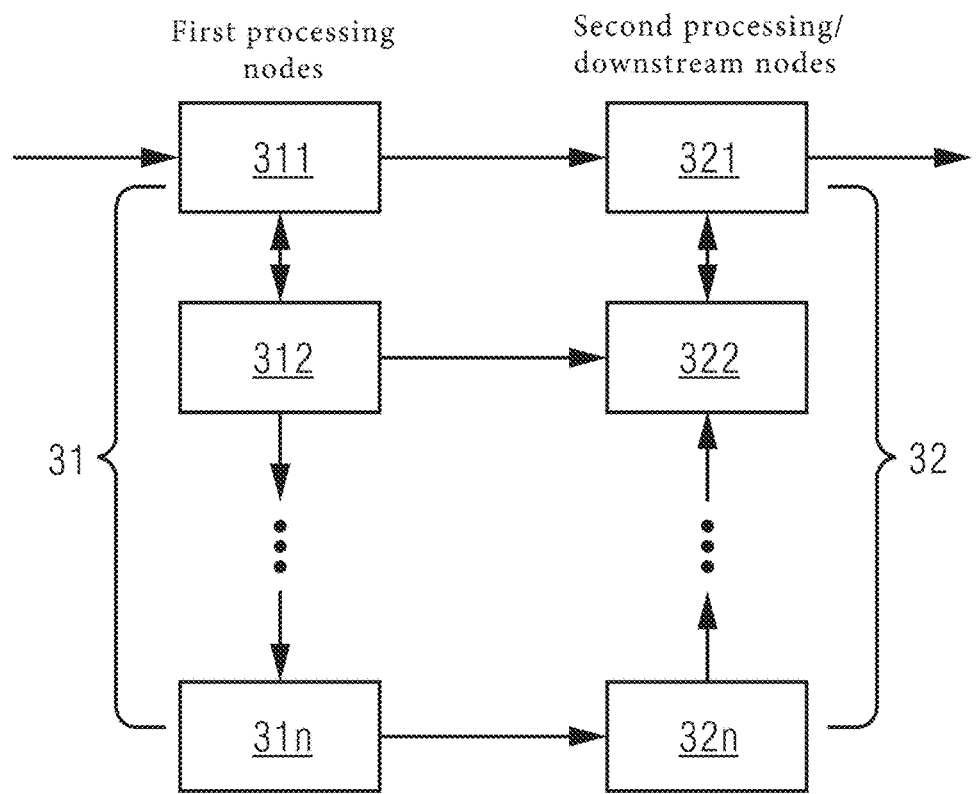
FIG. 3A is an example schematic diagram illustrating two processing paths of an image feature identifying module in accordance with various aspects of the present disclosure.

In examinations, small anomalies are often of greater importance than larger structures. In order to increase the resolution of extracted volume features and enable extraction of tiny volume features, the image feature identifying module 22 may process the 3D image through two processing paths, one path for capturing context information of each voxel (i.e., volume pixel, or the 3D counterpart of pixel) and the other path for increasing the resolution of volume features to precisely locate volume structures. FIG. 3A is a schematic diagram illustrating the two processing path of the image feature identifying module 22. As shown in FIG. 3A, the two processing paths include a first processing path 31 and a second processing path 32.

Figure 3B:
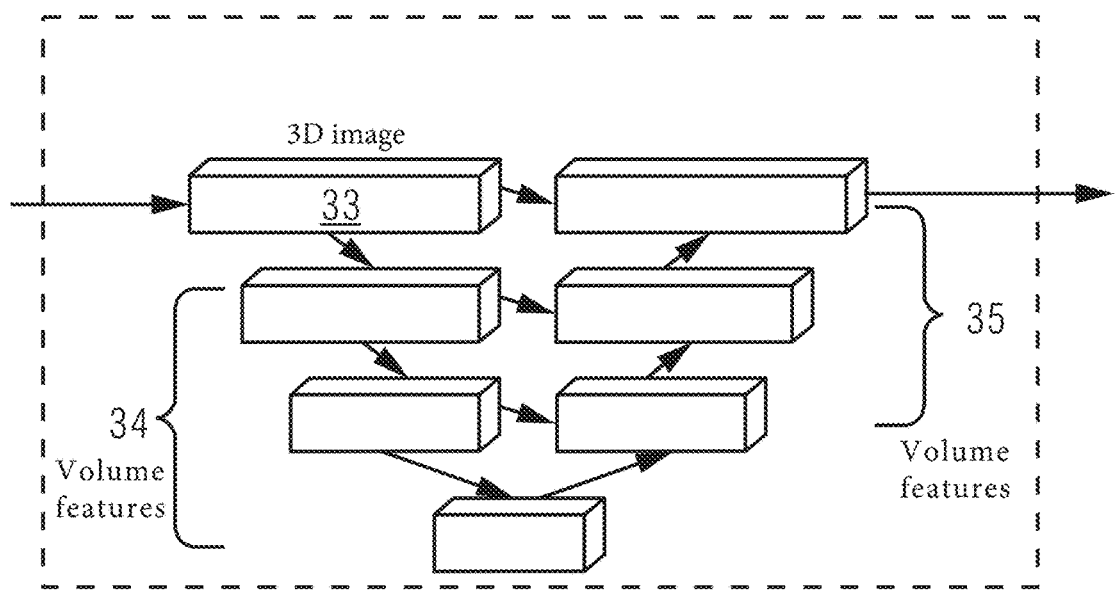
FIG. 3B is an example schematic diagram illustrating inputs and outputs of two processing paths of an image feature identifying module in accordance with various aspects of the present disclosure.

In the example as shown in FIG. 3A, the image feature identifying module 22 may input the 3D image to the first processing path 31. The first processing path 31 may include a plurality of successive first processing nodes 311, 312, . . . , 31n. Each of the first processing nodes may include a unit performing 3D convolution. For example, the 3D image may be inputted into the head node of the first processing path 31, i.e., first processing node 311. The node 311 performs its pre-defined operations on the image and outputs volume features to its downstream node 312, which performs its pre-defined operations on the volume features. Downstream refers to the direction in which image data flows. Similar procedures are performed by the downstream nodes until the end node of the first processing path 31, i.e., the first processing node 31n, performs its pre-defined operations on received volume features and generates its output volume features, which serve as the output of the first processing path 31. FIG. 3B is a schematic diagram illustrating inputs and outputs of the two processing paths 31 and 32. As shown in FIG. 3B, the top left side block 33 represents the 3D image inputted to the first processing path 31, and the lower left side blocks 34 represent the volume features outputted by the first processing nodes.

Volume features outputted by the first processing path 31 may be inputted to the second processing path 32. The second processing path 32 may include a plurality of successive second processing nodes 321, 322, . . . , 32n. Each of the second processing nodes may include a unit performing 3D up-convolution and take features outputted by a previous second processing node in the second processing path 32 and features outputted by one of the first processing nodes as input. In some examples, the previous node of a first node refers to a node which is the immediate upstream node of the first node. Upstream refers to the reverse direction of the direction in which image data flows.

In some examples, besides receiving first volume features from a previous node, a second processing node may also receive second volume features outputted by a corresponding node in the first processing path 31. The corresponding node refers to a first processing node whose output volume features have a resolution the same with or similar to that of the first volume features received by the second processing node. When the volume features outputted by the corresponding node have a resolution inconsistent with the resolution of the first volume features, the volume features may be processed to adjust the resolution for being consistent with the resolution of the first volume features. The volume features having the same resolution with that of the first volume features, which may or may not be processed through the resolution adjusting, are referred to as the second volume features inputted to the second processing node.

A second processing node may join the received first volume features with the second volume features to obtain joined features, and perform pre-defined operations on the joined features. As shown in FIG. 3B, the right side blocks 35 represent the volume features outputted by the second processing nodes. Each of the right side blocks 35 is merged with one of the left side blocks 34 to form the input of the next second processing node. Since the merged two blocks represent features included from different visual levels, joining them can enhance the discrimination capability of the image feature identifying module 22. The join operation may be applied to each voxel in the volume features, i.e., by joining a voxel in a first volume feature with a corresponding voxel in a second volume feature corresponding to the first volume feature (e.g., a second volume feature may be corresponding to the same portion of space in the input 3D image with the first volume feature, or the like). In various examples, the join operation may be one of: summation, maximization, concatenation, or the like. Each downstream second processing node can be benefitted from the guidance of output features of a corresponding first processing node, thus the end node of the second processing path 32 can have strong predictive power and highest identification resolution.

For example, the head node of the second processing path 32, i.e., the second processing node 32n, has no upstream node in the second processing path 32 and receives only the volume features outputted by the first processing path 31. The volume features outputted by the second processing node 32n are inputted to a downstream node in the second processing path 32 for processing. At second processing node 322, the input includes first volume features outputted by an upstream second processing node, and second volume features outputted by corresponding first processing node 312 in the first processing path 31. The end node of the second processing path 32, i.e., the second processing node 321, receives volume features outputted by upstream second processing node 322 and volume features outputted by corresponding first processing node 311 in the first processing path 31, processes the volume features, and output volume features which serve as the output of the second processing path 32.

All of the volume features outputted by each of the first processing nodes 311, 312, . . . , 31n and volume features outputted by each of the second processing nodes 321, 322, . . . , 32n are collected as the volume features identified by the image feature identifying module 22.

Operations performed by each of the processing nodes may be determined according to any suitable needs. In an example, operations performed by each first processing node in the first processing path 31 may include two 3D convolutions with a stride of two in order to enlarge the receptive field and enclose more contextual information, and each of the 3D convolutions may be followed by a batch normalization, an activation function such as a rectified linear unit (ReLu), and then a max pooling; operations performed by each second processing node in the second processing path 32 may include a 3D up-convolution with a stride of two in each dimension, followed by two 3D convolutions each followed by a batch normalization, an activation function such as a rectified linear unit (ReLu).

In an example, the image feature identifying module 22 may include a transition layer to manipulate the spatial grid size and feature dimension of output volume features so that the output volume features satisfy the input requirements of the report generating module 24.

By using the two processing path, one performing 3D convolutions and the other performing 3D up-convolutions, tiny volume features can be identified from the 3D image with increased resolution and accuracy.

In addition to the volume features obtained by the image feature identifying module 22, the semantic attribute predicting module 23 is included in the report generating apparatus 21 to obtain explicit semantic representations of attributes of 3D images. The semantic attribute predicting module 23 may identify semantic representations of a number of semantic elements which are determined the most likely to be associated with the 3D image from a pre-defined element set of semantic elements. For example, the semantic attribute predicting module 23 may identify the top N semantic elements predicted to be associated with the 3D image by calculating the probability of being associated with the 3D image for each semantic element in the element set. The element set may include a plurality of semantic elements mined from reports associated with the annotated 3D images which serve as the training dataset. In some examples, the semantic elements may be stored in the form of semantic representations, i.e., the element set may include semantic representations of the semantic elements.

In an example, in order to identify tiny structures like a calcium in a 3D image, the semantic attribute predicting module 23 may perform the following procedures: performing objectness detection to produce a set of candidate object 3D bounding boxes, selecting a much smaller number of candidate bounding boxes as hypotheses using a hypotheses extraction method, grouping the candidate bounding boxes into m clusters using a cluster algorithm, and selecting k hypotheses with the highest probabilities from each of the m clusters, in which m and k are positive integers. Together with the 3D image, there are m*k+1 hypotheses for the 3D image. The selected hypotheses may be fed into the second ML module. In some examples, the second ML module may be a shared convolutional neural network (CNN), or the like. The second ML module may generate a prediction vector for each inputted hypothesis. Each prediction vector includes a plurality of predicted semantic representations and probability values of the predicted semantic representations. A cross hypothesis max pooling may be applied to integrate the outputted prediction vectors into a single prediction vector. The above is merely an illustrative example. In other examples, the semantic attribute predicting module 23 may be implemented in alternative manners.

In various examples, the semantic attribute predicting module 23 may identify not only representations of the names of structures illustrated in the 3D image, such as the name of a volume structure, the name of an abnormality, or the like, but also representations of attributes associated with volume structures in the 3D image. The attributes may include various types of information, e.g., descriptive statements (e.g., adjectives), negations, uncertain statements, suspicious findings, conclusions, recommendations, or the like.

In various examples, semantic representations of attributes associated with volume structures in 3D image may be identified using a multi-label classification module of the second ML module. The multi-label classification module may be trained using the annotated 3D images and semantic representations obtained from the reports associated with the annotated 3D images.

In some examples, a plurality of first semantic representations of nouns associated with the volume structures in the 3D image may be identified using first parameters of the second ML module. The first parameters of the second ML module may be determined using annotations of volume structures in the annotated 3D images.

In some examples, a plurality of second semantic representations of descriptive statements associated with the volume structures may be identified using the second parameters of the second ML module. The second parameters of the second ML module may be determined using semantic representations obtained from the reports associated with the annotated 3D images.

For example, the second ML module may be trained through at least two phases to determine the first parameters and the second parameters. At a first phase, the second ML module may be pre-trained using the annotated 3D images in a way similar to the training of the first ML module, to determine the first parameters for identifying volume structures in a 3D image. At a second phase, the second ML module may be trained further using the semantic representations of semantic elements extracted from the reports and the annotated 3D images, to determine the second parameters for identifying other information associated with a 3D image, e.g., descriptive statements, uncertainty statements, or the like. In the second phase, the second ML module may be trained by using the annotated 3D images as input and the reports as the ground truth.

Figure 4:
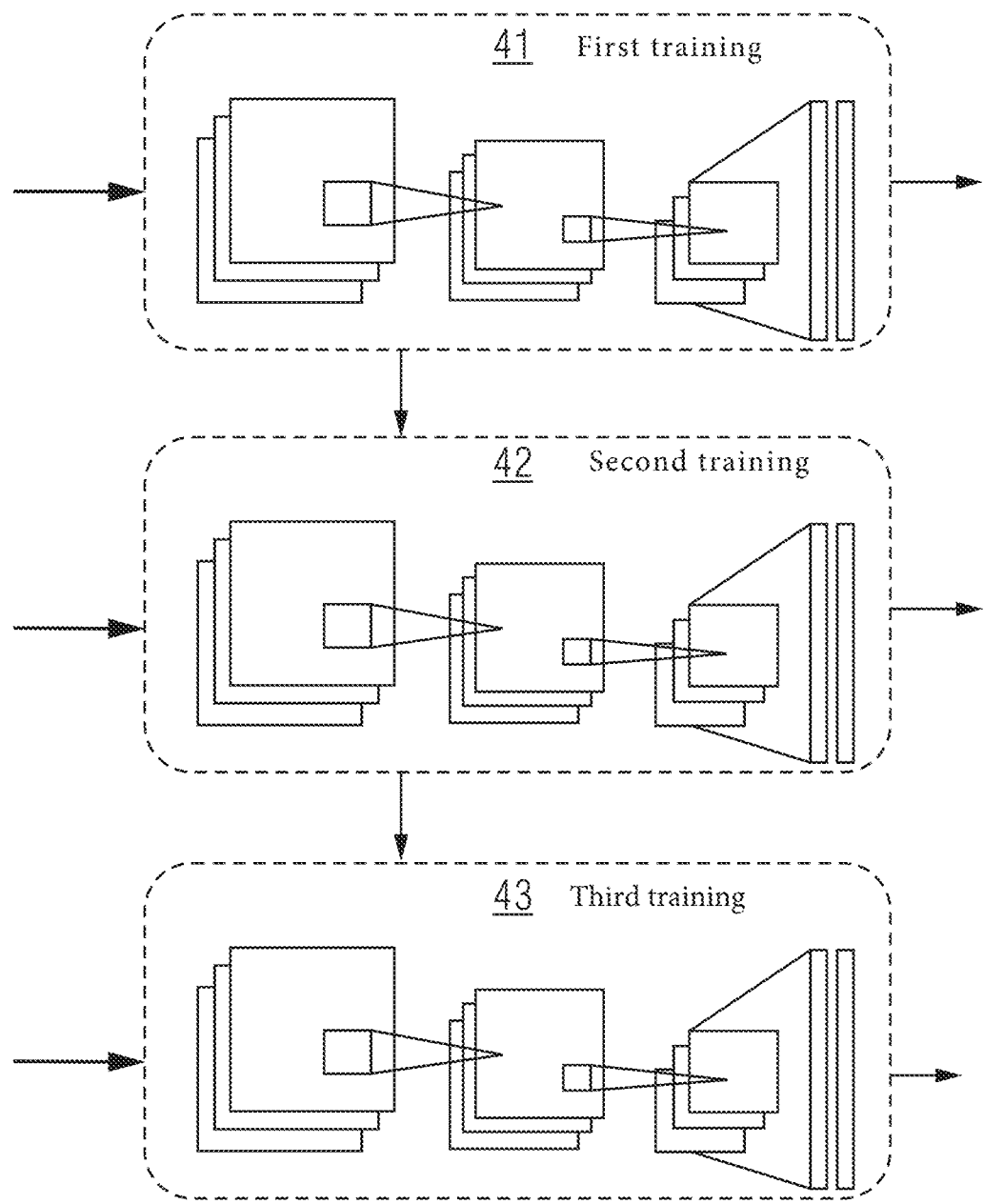
FIG. 4 is an example schematic diagram illustrating training of a second ML module in accordance with various aspects of the present disclosure.

The above is merely an example of the training of the second ML module. In various examples, the second ML module may be trained in other manners. For example, as shown in FIG. 4, the second ML module may include a CNN, and the training of the CNN may include a first training 41, a second training 42, and a third training 43.

During the first training 41, the second ML module may be trained using the annotated 3D images and annotations of large structures (e.g., mechanical structure or part, a body part, or the like), so as to enable the second ML module to identify the large structures in an input image. The annotations of a large structure may be obtained from marks made in an image processing workstation by an expert on the annotated 3D images, or obtained from a template defining the 3D region occupied by the structure, e.g., a heart mask, or a brain mask, or the like, provided by a medical image processing workstation. The first training 41 may be regarded as the process of solving an image segmentation problem, and image segmentation losses 44 may be calculated using the output of the CNN and the annotations of the large structures, and used for adjusting the parameters.

During the second training 42, the second ML module may be trained using the annotated 3D images and annotations of tiny structures, so as to enable the second ML module to identify the tiny structures in an input image. The annotations of the tiny structures may be obtained from marks made in an image processing workstation by an expert on the annotated 3D images, or obtained from a template defining the 3D region of the tiny structures, e.g., a calcium mask, or the like, generated by a medical image processing workstation. The second training 42 may also be regarded as the process of solving an image segmentation problem, and image segmentation losses 45 may be calculated using the output of the CNN and the annotations of the tiny structures, and used for adjusting the parameters.

During the third training 43, the second ML module may be fed with the annotated 3D images and corresponding reports. The third training 43 may be regarded as a process of solving a multi-label classification problem. During the third training 43, a list of representations of semantic elements obtained from each report through a NLP process such as TF-IDF is used as the ground truth. The semantic elements may include names and properties of various structures used in the reports. The use of report language elements guarantees that the most salient attributes of an image can be extracted. Classification losses 46 may be calculated using the output semantic representations and ground truth, and used for adjusting the parameters of the second ML module.

Figure 5:
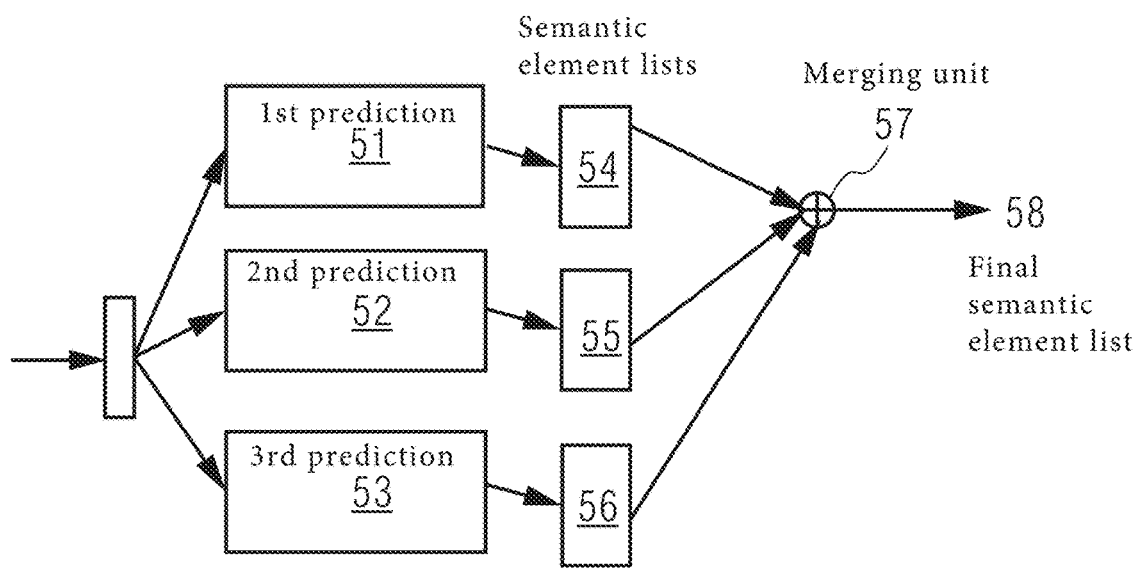
FIG. 5 is an example schematic diagram illustrating a predicting process of a second ML module in accordance with various aspects of the present disclosure.

In some examples, the second ML module may use a plurality of prediction methods. Each prediction method may output a list of predicted semantic elements. For example, as shown in FIG. 5, the second ML module may include a first prediction method 51, a second prediction method 52, and a third prediction method 53. The prediction methods 51, 52, 53 may all be trained using the annotated 3D images and the reports. During a report generating process, a 3D image may be inputted to each of the prediction methods, and three semantic element lists 54, 55, 56 may be outputted. Each predication method may also output a probability value of each semantic element in the lists. The probability value represents the probability that the semantic element is related to the 3D image as predicted by the prediction method. The predicted semantic elements may include nouns such as "stenosis," and adjectives such as "severe" as well. The lists 54, 55, 56 may be combined using a merging unit 57 according to a pre-defined method to generate a final semantic element list 58. The list 58 may include semantic elements or semantic representations of the semantic elements, and may serve as the output of the semantic attribute predicting module 23.

In some examples, only key words may be extracted from the reports and used in training the second ML module, so that only meaningful and important semantic features are extracted by the second ML module from an input 3D image. In some examples, the reports may be processed through a NLP technique to extract semantic representations of a plurality of words in the reports. In other examples, the second ML module may be trained using the annotated 3D images and the reports following other approaches as needed.

By training the second ML module using reports associated with the annotated 3D images, not only names of structures, but also descriptive statements associated with the structures, can be extracted by the second ML module from a 3D image to guide subsequent generation of the report in the third ML module. As such, it can be ensured that the generated report can cover most of important features of the 3D image, and can provide more information than just a list of names of structures and abnormalities.

In various examples, after the volume features and semantic representations are obtained from the 3D image, semantic elements associated with the volume features may be determined using trained parameters of the third ML module, and a report may be generated using the semantic elements together with the semantic representations obtained by the second ML module. The report may be generated in various methods.

In some examples, the report may be generated by arranging semantic elements associated with the volume features and semantic elements corresponding to the semantic representations using trained parameters of the third ML module to form a report conforming to natural language rules.

In some other examples, the report may be generated element-by-element (e.g., word-by-word, segment-by-segment, sentence-by-sentence, or the like) in a series of time steps, and a semantic element is decided in each time step using the third ML module according to the volume features, the semantic representations and at least one semantic element selected in previous time steps. For example, the third ML module may include a temporal neural network, e.g., a Recurrent Neural Network (RNN) with a Long Short-Term Memory (LSTM) cell, or the like. At block S13, the report generating module 24 may select a semantic element from a pre-defined element set at each time step based on parameters of the third ML module, the volume features, the semantic representations and a semantic element selected in a previous time step, and add the selected semantic element into the report.

The element set is a collection of semantic elements that are likely to appear in an analysis report, e.g., a vocabulary, a sentence collection, or the like. In some examples, an element set may be generated for the specific type of examination, e.g., for a specific part concerned by the examination, for a specific type of abnormality concerned by the examination, or the like. For example, the element set may be generated using semantic elements from reports generated or confirmed by field experts, or from a field-specific dictionary, or the like.

Figure 6A:
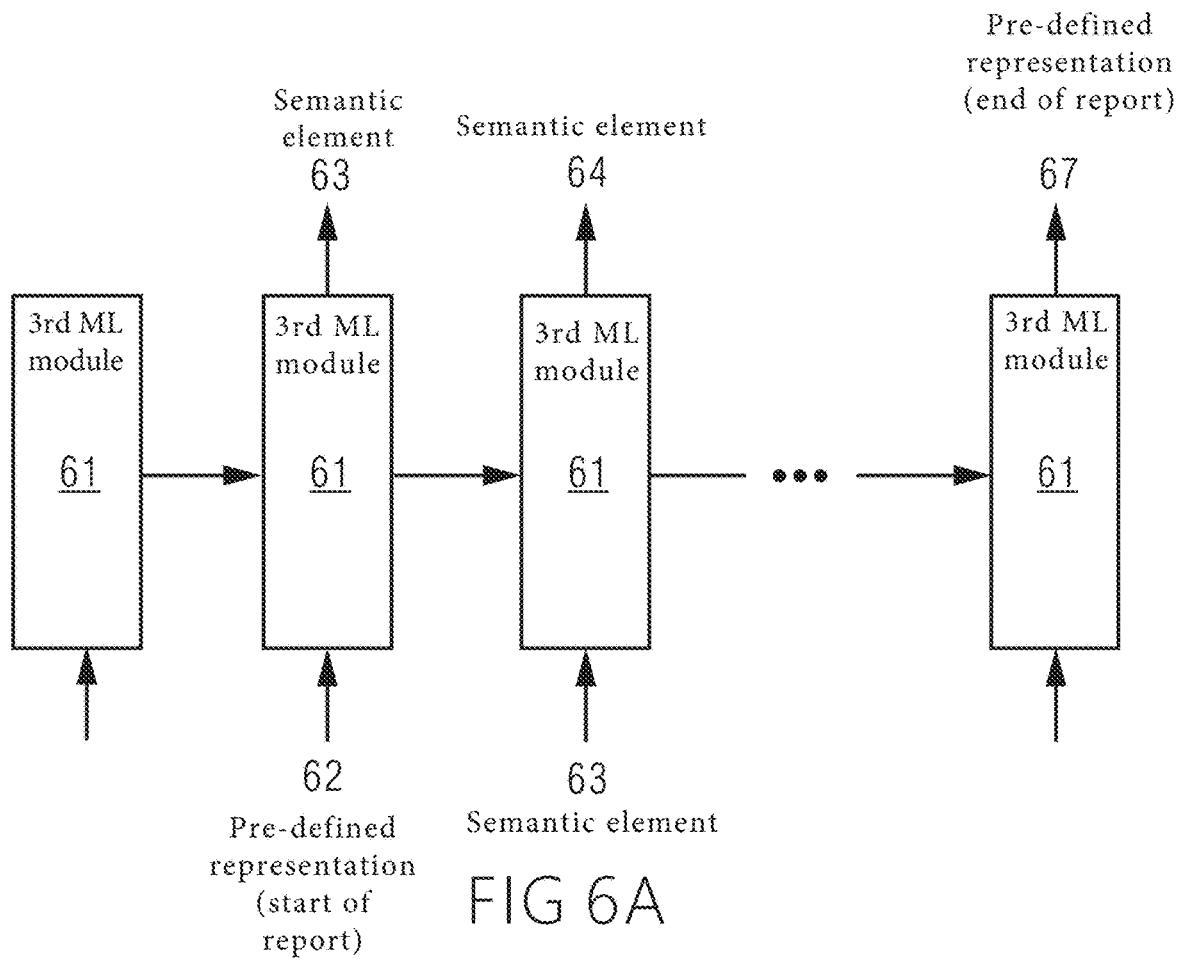
FIG. 6A is an example schematic diagram illustrating a process of generating a report in accordance with various aspects of the present disclosure.

FIG. 6A is a schematic diagram illustrating a process of generating a report by deciding a semantic element in each time step. As shown in FIG. 6A, the volume features obtained by the image feature identifying module 22 and the semantic representations obtained by the semantic attribute predicting module 23 may be inputted into the third ML module 61. At a first time step, a pre-defined representation 62 indicating "start of report" may be inputted into the third ML module 61, which selects a first semantic element 63 from a pre-defined element set based on the volume features, the semantic representations and trained parameters of the third ML module 61. At a second time step, the semantic element 63 may be inputted into the third ML module 61, which then selects a second semantic element 64 from the pre-defined element set. The process may be repeated until a pre-defined representation 67 indicating "end of report" is selected. All of the selected semantic elements form the generated report.

Figure 6B:
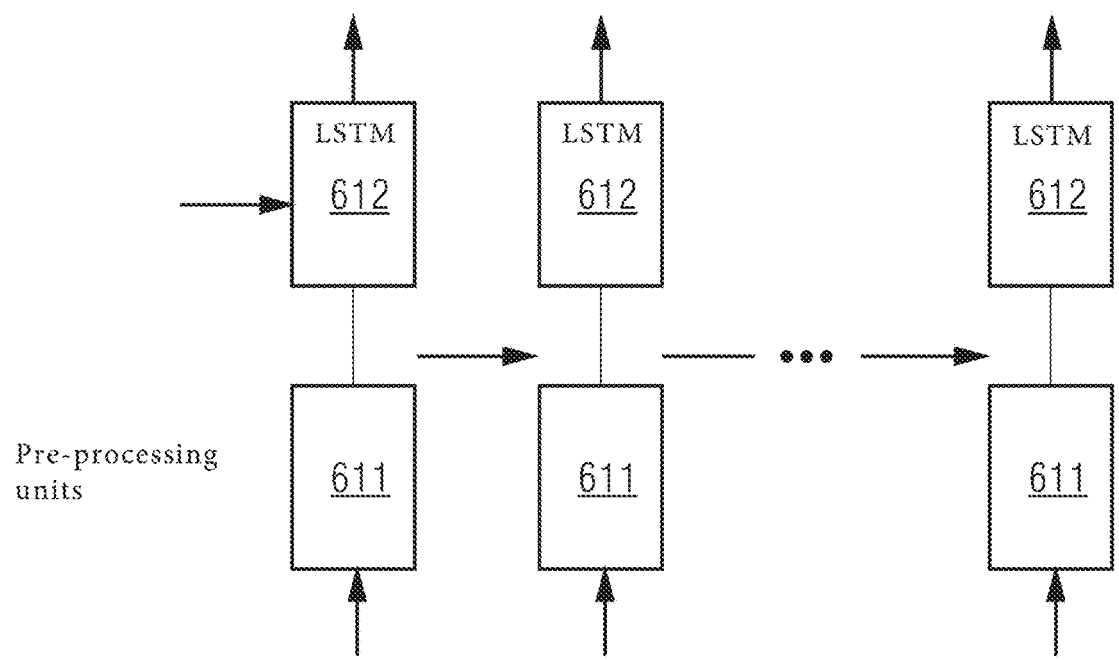
FIG. 6B is an example schematic diagram illustrating a process of generating a report in accordance with various aspects of the present disclosure.

In some examples, the third ML module 61 may include a temporal neural network unit and an input pre-processing unit which blends the semantic representations obtained by the semantic attribute predicting module 23 with a semantic element from the element set to generate an input of the temporal neural network unit in each time step, so that the semantic representations can be considered in the report generating process. FIG. 6B is a schematic diagram illustrating a process of generating a report by deciding a semantic element in each time step. As shown in FIG. 6B, the third ML module may include an input pre-processing unit 611 and a LSTM unit 612, which serves as a temporal neural network unit.

The volume features obtained by the image feature identifying module 22 may be inputted into the LSTM unit 612 to initialize the first hidden state of the LSTM unit 612. At each time step, the input pre-processing unit 611 may integrate the semantic representations obtained by the semantic attribute predicting module 23 with a semantic representation to be inputted into the LSTM unit 612, and provide the integrated data as the input of the LSTM unit 612. The input pre-processing unit 611 may process the semantic representations using a pre-defined processing method to integrate the semantic representations. The processing method may be a concatenation method, a linear processing method, or the like. For example, a semantic representation of a semantic element may be a vector of real numbers, and the semantic representations obtained by the semantic attribute predicting module 23 may be a list of vectors Vsa(I). At the (i-th) time step, the input pre-processing unit 611 may integrate a semantic representation S(i−1) with Vsa(I) using a pre-defined function ƒ(S(i−1), Vsa(I)), and input the result of f(S(i−1), Vsa(I)) into the LSTM unit 612 which generates a semantic representation S(i), in which i is a positive integer.

For the $1^{st}$ time step, S0 may be a pre-defined representation 62 indicating "start of report"; for following time steps, S(i−1) may be a semantic representation selected by the LSTM unit 612 in a previous time step. In an example, the function ƒ(S(i−1), Vsa(I)) may be a concatenation function which joining vector S(i−1) and vectors in Vsa(I) end-to-end to form a longer vector, e.g., a vector having P*(Q+1) elements, where P is the number of elements in each semantic representation, Q is the number of semantic representations obtained by the semantic attribute predicting module 23.

In another example, the function ƒ(S(i−1), Vsa(I)) may be a linear processing function which generates a vector of the same length with a semantic representation while each element in the vector is obtained by combining corresponding elements of S(i−1) and Vsa(I). For example, the linear processing function may be α·S(i−1)+(1−α)·Vsa(I), where α is a pre-determined hyper parameter weight. The integrated data obtained by the input pre-processing unit 611 which contains predicted semantic information of the 3D image may be inputted into the LSTM unit 612. The LSTM unit 612 may make a selection of a semantic element from the vocabulary based on the integrated data. The process may be repeated until a pre-defined representation indicating "end of report" is selected. In various examples, the LSTM unit may adopt any feasible LSTM structure, such as a bi-directional LSTM, a multi-layer LSTM, or the like.

Since the third ML module has been trained using the annotated 3D images and associated reports, parameters of the third ML module are capable of identifying semantic elements associated with volume features and arrangement orders of semantic elements. Based on the volume features obtained from the 3D image and at least one semantic element previously decided and added to the report, the report generating module 24 may decide the semantic element to be added to the report in the current time step with the assistant from the semantic representations obtained by the semantic attribute predicting module 23. By generating a semantic element at each time step based on already generated report content, contents of the generated report can be well arranged with strong ties between elements.

According to various examples, at each time step, the report generating module 24 may select the semantic element having the largest probability given the current situations. The current situations may include context of the report, the volume features that have been described or have not been described, natural language rules, or the like. In some examples, the semantic attribute predicting module 23 may also obtain a probability value corresponding to each of the semantic representations identified. A probability value of a semantic representation represents the probability that the semantic representation is associated with the 3D image. The report generating module 24 may use the probability value obtained by the semantic attribute predicting module 23 to decide the next semantic element to be added to the report.

In an example, the semantic elements are words, the element set is a pre-defined vocabulary, and the report generating module 24 may obtain a probability value of each of the semantic representations determined by the second ML module, calculate a conditional probability value of each semantic element in the vocabulary given semantic elements selected in previous time steps based on the probability value of each of the semantic representations and the parameters of the third ML module, and select the semantic element according to the conditional probability value of each semantic element in the vocabulary.

For example, suppose that $\{S_1, \ldots, S_L\}$ is the pre-defined vocabulary. The third ML module may calculate a log-likelihood of each of words given the context words $S_{1:\ t-1}$ and the 3D image I according to Equation 1 below:

$$\log p(S|V_{sa}(I)) = \Sigma_1^L \log p(S_t|S_{1:\ t-1}, V_{sa}(I)) \quad \text{Eqn. 1}$$

In the above Eqn. 1, $p(S_t|S_{1:\ t-1}, V_{sa}(I))$ represents the conditional probability of the word $S_t$ given the semantic representation vector $V_{sa}(I)$ and previously selected words $S_{1:\ t-1}$.

For example, the vocabulary may include words obtained from reports generated or confirmed by field experts, a pre-defined first representation representing "the start of report", and a pre-defined second representation representing "the end of report". At the beginning, the report generating module 24 may create a report. The newly created report may be initiated to be blank, i.e., having no content. The report generating module 24 may add the first representation into the report, and calculating the probabilities of words from the vocabulary appearing after the first representation based on the volume features, the semantic representations, and the parameters of the third ML module. If the word "There" is decided to be the most likely word after the first representation, "There" is added to the report. Then, based on natural language rules, the word "is" and "are" have large probability to appear after "There". According to the findings that the volume features includes a volume feature identified as a tumor and that the semantic representations obtained by the semantic attribute predicting module 23 include the semantic representation of "tumor", the report generating module 24 may determine using the parameters of third ML module that the calculated probability of the word "is" is larger than that of the word "are", a decision is made that the word "is" is to be added to the report. Similarly, the words "a" and "tumor" may be added to the report in successive time steps according to calculation results of the third ML module. The procedures may be repeated to continuously add other words and sentences to the report until the second representation representing "the end of report" is added to the report to conclude the process.

By taking the probabilities of the semantic representations into consideration and selecting a semantic element according to the conditional probability value, the selection process can be more efficient and accurate.

In various examples, the report generating apparatus may also include a training module for training the first ML module, the second ML module, and the third ML module.

According to some examples, the ML modules, i.e., the first ML module, the second ML module, and the third ML module may be trained individually. According to some other examples, the ML modules may, alternatively or additionally, be trained jointly, and information generated during the joint training may be exchanged between ML modules. During joint training of the ML modules, parameters of at least one of the ML modules may be adjusted based on feedback information from another of the ML modules so as to achieve better overall performances.

For example, the first ML module may be adjusted during joint training according to feedback from the third ML module. Specifically, the training process of the first ML module may be performed by a training module of the report generating apparatus as follows.

The training module may determine parameters of the first ML module using annotations of volume structures in the annotated 3D images, and this procedure is referred to as the pre-training of the first ML module. Through the pre-training, the first ML module is capable of extracting volume features from a 3D image using the parameters.

Then, parameters of the third ML module may be determined using the reports, and results generated by the first ML module and the second ML module in a joint training process. During the joint training process, the third ML module may take the volume features obtained using the first ML module and the semantic representations obtained using the second ML module as the input, and the reports associated with the annotated 3D images as the global ground truth to determine the parameters of the third ML module.

While determining the parameters of the third ML module, the parameters of the first ML module may be adjusted using feedback generated by the third ML module. The third ML module may generate a predicted output based on the input, uses the global ground truth as the expected output, and propagates the error between the predicted output and the expected output backwards along the processing path to adjust the parameter of each processing node, e.g., a perceptron or a neuron. The backward propagated information may be propagated to the first ML module, and the first ML module uses the backward propagated information as feedback from the third ML module to adjust the parameters of the first ML module. For example, the third ML module generates a word for an annotated 3D image in a time step, obtains a word from a report associated with the annotated 3D image, and generates feedback information using the two words which is propagated backwards to adjust parameters of the third ML module and the parameters of the first ML module.

As such, through the backward propagation between ML modules, the overall performance of the report generating apparatus can be improved.

The first ML module and the second ML module are both required to identify volume features in a 3D image, thus have some shared parameters. In some examples, it is unnecessary to train the first ML module and the second ML module respectively, and instead, one of the first ML module and the second ML module may be trained, and the trained parameters may be shared with the other. For example, the training module may train one of the first ML module and the second ML module using the annotations of the volume structures in the annotated 3D images to determine parameters of the one of the first ML module and the second ML module, and initialize the parameters of the other of the first ML module and the second ML module using the parameters of the one of the first ML module and the second ML module obtained through the training. As such, resources and time needed for the training can be reduced.

Training of the ML modules requires annotated 3D images and associated reports. Large amount data annotation requires expert knowledge and is time consuming. According to various examples, the annotations and reports associated with 3D images for training may be obtained from history examination records, without requiring additional manual annotation work.

In an example, the report generating apparatus may include a data obtaining module. The data obtaining module may obtain history examination records generated by an image processing workstation, e.g., the image processing workstation 25. The history examination records may include: history 3D images, category information of the history 3D images generated by the image processing workstation, marks on the history 3D images confirmed by an expert, and history analysis reports associated with the history 3D images, or the like.

The history 3D images are images generated during daily examination routine. The history analysis reports are reports generated for the history 3D images during daily examination routine and confirmed by an expert.

Annotations associated with history 3D images may include category information and marks associated with the history 3D images.

The category information may be generated by the image processing workstation. For example, when an expert performs an examination, he/she may select category information for the image generated in the workstation, e.g., the clinical department that prescribed the examination, the examined part, the abnormality to be inspected, or the like.

When an expert reads an image in the workstation, he/she may mark certain parts or abnormalities using tools provided by the workstation for purposes such as zooming, measuring, or the like. The manually added marks on the history 3D images may be used as structure annotations.

Some workstations also provide masks for a part. A mask is a template defining the 3D region occupied by the part. The workstation may use the mask selected by the expert to segment the part from the 3D image, so that only the part in the image are displayed, and the other portions are blanked out to highlight the part. The mask provided by the workstation or selected by the expert for an image may also be used as structure annotations associated with the image, i.e., the annotations of the examined part.

As such, the history 3D images may be provided as the annotated 3D images, the marks (sometimes together with the category information) may be provided as annotations of the annotated 3D images, and the history analysis reports may be provided as the reports associated with the annotated 3D images. By obtaining the annotated 3D images and associated reports from history examination records provided by an image processing workstation, the ML modules can be trained without requiring additional annotation work.

Figure 7:
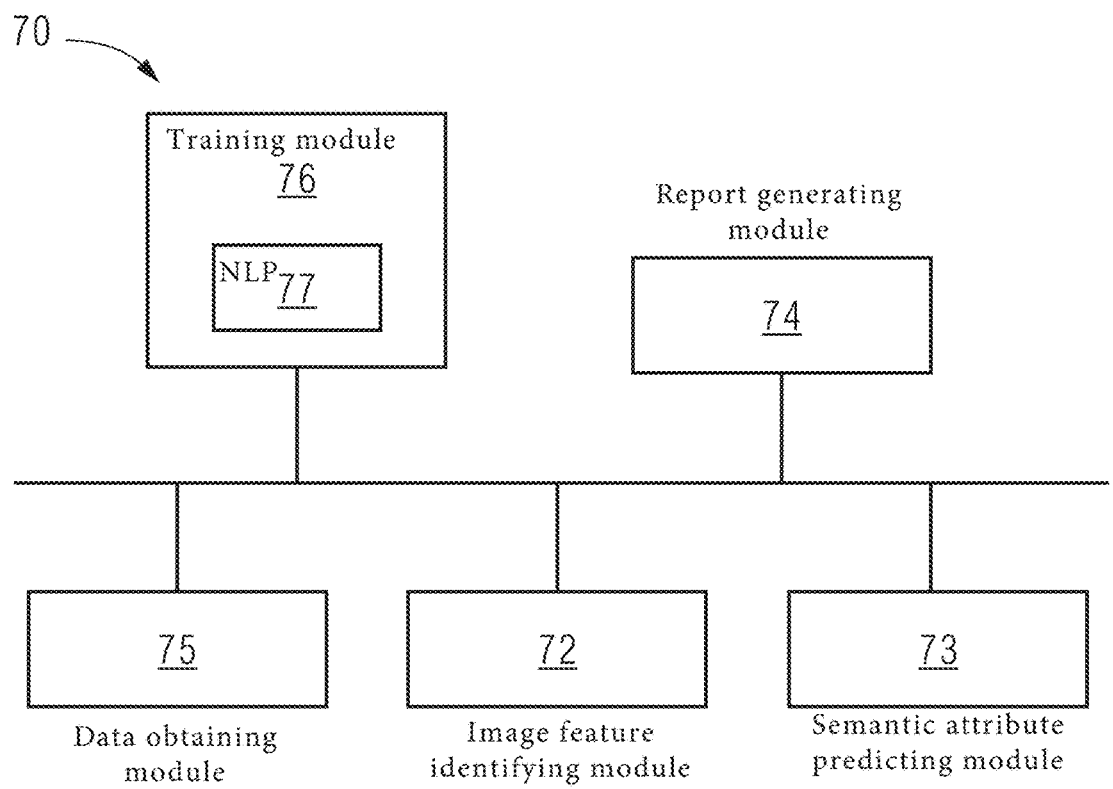
FIG. 7 is an example schematic diagram illustrating a report generating apparatus in accordance with various aspects of the present disclosure.

The following is another example of the report generating apparatus. As shown in FIG. 7, the report generating apparatus (or report generating circuitry or a report generator) 70 may include an image feature identifying module 72, a semantic attribute predicting module 73, a report generating module 74, a data obtaining module 75 and a training module 76. The report generating apparatus 70 may be implemented using any suitable number and/or type of processors, hardware components, software components, or a combination of any of these In this example the report generating apparatus 70 adopts a CNN-RNN structure as the basic structure for generating reports. The image feature identifying module 72 uses a CNN in the first ML module for extracting volume features. The report generating module 74 uses a RNN in the third ML module for generating reports. The semantic attribute predicting module 73 provides additional guidance to the CNN-RNN structure by providing semantic representations predicted to be related with an input 3D image.

The data obtaining module 75 may obtain annotated 3D volume images and related reports as the training dataset. The data obtaining module 75 may obtain history image annotation results produced by an image processing workstation. For example, in the scenario of cardiac calcium score analysis, the data obtaining module 75 may extract history calcium annotation results and heart masks from an image processing workstation. The annotation results are clinically and routinely generated by the image processing workstation and confirmed by a radiologist. The data obtaining module 75 may provide the annotation results as the ground truth used in training. The training dataset may include 3D images, image annotations and associated reports, which are all from clinically generated history data. This makes it possible to train the ML modules with a large amount of data and annotations without additional heavy annotation work of drawing bounding boxes on structures, mapping words to bounding boxes and the like.

The training module 76 may use the training data set to train the ML modules. The training module 76 may include a NLP processing module 77 for converting natural language elements in the reports into semantic representations of semantic elements which are then used in training. The semantic representations may be numbers or strings or vectors, thus allow a computing device to handle the semantic information.

The training module 76 may train the image feature identifying module 72 in two steps. In the first training step, the image feature identifying module 72 is trained alone by taking training 3D images (i.e., the annotated 3D images) as input and image annotations as ground truth. In the second training step, the image feature identifying module 72 is trained together with the report generating module 74, and the training 3D images are the input and the reports are the overall ground truth. During the second training step, parameters of the image feature identifying module 72 may be adjusted by back propagation.

Parameters of the image feature identifying module 72 determined from the first training step may be used to initialize the semantic attribute predicting module 73. Then the training module 76 may train the semantic attribute predicting module 73 using semantic representations of semantic elements obtained by the NLP processing module 77 from the reports.

In the second training step, volume features identified from the 3D images by the image feature identifying module 72, semantic prediction results (may include predicted representations and associated probability values) generated from reports by the semantic attribute predicting module 73 may also be fed into the report generating module 74. The volume features may be used to initialize the first hidden state of the RNN of the report generating module 74. In addition, the report generating module 74 may use the semantic prediction results as the external guide for the RNN in generating each word of the report, e.g., in calculating the conditional probability value (e.g., the log-likelihood) of each word.

During a report generating process (e.g., when testing the report generating apparatus 70, or when the report generating apparatus 70 is put into use), an input 3D image is inputted into the image feature identifying module 72 to generate the volume features, and into the semantic attribute predicting module 73 to generate the semantic prediction results. The volume features are inputted into the report generating module 74 to initialize the RNN's first hidden state. Then the RNN produces the report by generating one word at each time step conditioned on a previous hidden state, the previously generated word, and semantic prediction results. As the hidden state in the RNN evolves over time, words are selected from the vocabulary one-by-one according to a probability vector controlled by the hidden state. Each generated word is fed back into the RNN in the next time step as part of the input, which drives transition of the hidden state. The semantic prediction results serve as the external guide for the RNN in the process.

According to various examples, the report generating apparatus may automatically generate a report for a 3D image, e.g., for a heart calcium CT image, or the like.

Moreover, although not shown in FIG. 7 for purposes of brevity, the report generating apparatus 70 may also include or otherwise access any suitable type of storage medium, which may be implemented as a non-transitory computer-readable storage medium, for example (e.g. non-volatile or volatile memory). The non-transitory computer-readable storage medium may store or otherwise include computer-readable instructions executable by one or more processors and/or components of the report generating apparatus 70 processor to carry out the methods, functionality, and/or techniques described in the various examples of the embodiments as discussed herein and/or with reference to one or more of the FIGS. 1, 2, 3A, 3B, 4, 5, 6A, 6B, 7, etc.

The foregoing description, for the purposes of explanation, has been described with the reference to specific examples. However, the illustrative discussions above are not intended to be exhaustive or to limit the present disclosure to the precise forms disclosed. Many modifications and variations are possible in view of the above teachings. The examples were chosen and described in order to best explain the principles of the present disclosure and its practical applications, to thereby enable others skilled in the art to best utilize the present disclosure and various examples with various modifications which are suited to the particular use contemplated.

The various functional blocks, apparatuses, modules, units, components of physical or functional units, etc., as shown in the drawings and described herein may be implemented as any suitable number and type of computer processors, hardware components, the execution of software algorithms, or combinations thereof, and thus may alternatively be referred to as a "unit," "system," "circuitry," or a "device."

What is claimed is:

1. A method of generating reports of three dimensional (3D) images, comprising:
   identifying, via a report generator, a plurality of volume features in a 3D image using a first machine learning (ML) processor that is trained with annotated 3D images;
   identifying, via the report generator, a plurality of semantic representations associated with the 3D image using a second ML processor that is trained with the annotated 3D images and reports associated with the annotated 3D images; and
   generating, via the report generator, a report of the 3D image based on the identified plurality of volume features and the identified plurality of semantic representations using a third ML processor that is trained with the annotated 3D images, the reports associated with the annotated 3D images, and outputs generated by the first ML processor and the second ML processor using the annotated 3D images and the reports associated with the annotated 3D images.

2. The method of claim 1, wherein identifying the plurality of semantic representations associated with the 3D image comprises:
   identifying semantic representations of attributes associated with volume structures in the 3D image using a multi-label classification processor of the second ML module, the multi-label classification processor being trained using the annotated 3D images and the identified plurality of semantic representations obtained from the reports associated with the annotated 3D images.

3. The method of claim 1, wherein generating the report of the 3D image comprises:
   selecting a semantic element from a pre-defined element set at each one of a plurality of time steps using the third ML module, the volume features, the identified plurality of semantic representations, and the semantic element being selected in a previous time step from among the plurality of time steps; and
   adding the semantic element selected in the previous time step into the report.

4. The method of claim 3, wherein the pre-defined element set is a pre-defined vocabulary, and
   wherein selecting the semantic element from the pre-defined element set comprises:
   calculating a conditional probability value of each semantic element in the pre-defined vocabulary using (i) semantic elements selected in previous time steps from among the plurality of time steps, and (ii) the identified plurality of semantic representations using the third ML module; and
   selecting the semantic element according to the conditional probability value of each semantic element in the vocabulary.

5. The method of claim 1, further comprising:
   determining parameters of the first ML processor using annotations of volume structures in the annotated 3D images;
   determining parameters of the third ML processor using the annotated 3D images, the reports, and results generated from processing the annotated 3D images by the first ML processor and the second ML processor; and
   adjusting the determined parameters of the first ML processor using feedback generated by the third ML processor while determining the parameters of the third ML processor.

6. The method of claim 1, further comprising:
   determining parameters of one of the first ML processor and the second ML processor by training one of the first ML processor and the second ML processor using annotations of volume structures in the annotated 3D images; and
   initializing the other one of the first ML processor and the second ML processor using the determined parameters.

7. The method of claim 1, further comprising:
   obtaining history examination records generated by an image processing workstation, the history examination records comprising history 3D images, marks on the history 3D images generated in the image processing workstation, and history analysis reports associated with the history 3D images;
   providing the history 3D images as the annotated 3D images;
   providing the marks as annotations of the annotated 3D images; and
   providing the history analysis reports as the reports associated with the annotated 3D images.

8. The method of claim 1, wherein generating the report of the 3D image comprises:
   selecting, via the third ML module, a semantic element from a pre-defined element set, which includes a pre-defined vocabulary, at each one of a plurality of time steps using the volume features, the identified plurality of semantic representations, and the pre-defined element set by selecting the semantic element according to a calculated conditional probability value of each semantic element in the pre-defined vocabulary.

9. The method of claim 1, further comprising:
   adjusting determined parameters of the first ML processor using feedback generated by the third ML processor.

10. The method of claim 9, further comprising:
    adjusting the determined parameters of the first ML processor using the feedback generated by the third ML processor while determining parameters of the third ML processor.

11. A report generator configured to generate reports of three dimensional (3D) images, comprising:
    image feature identifying circuitry configured to identify a plurality of volume features in a 3D image using a first machine learning (ML) processor that is trained with annotated 3D images;
    semantic attribute predicting circuitry configured to identify a plurality of semantic representations associated with the 3D image using a second ML processor that is trained with the annotated 3D images and reports associated with the annotated 3D images; and
    report generating circuitry configured to generate a report of the 3D image based on the identified volume features and the identified plurality of semantic representations using a third ML processor that is trained with the annotated 3D images, the reports associated with the annotated 3D images and outputs generated by the first ML processor and the second ML processor using the annotated 3D images and the reports associated with the annotated 3D images.

12. The apparatus of claim 11, wherein the semantic attribute predicting circuitry is configured to identify semantic representations of attributes associated with volume structures in 3D image using a multi-label classification processor of the second ML module, the multi-label classification processor being trained using the annotated 3D images and identified plurality of semantic representations obtained from the reports associated with the annotated 3D images.

13. The apparatus of claim 11, wherein the report generating circuitry is configured to:
select a semantic element from a pre-defined element set at each one of a plurality of time steps using the third ML module, the volume features, the identified plurality of semantic representations, and the semantic element being selected in a previous time step from among the plurality of time steps; and
add the selected semantic element selected in the previous time step into the report.

14. The apparatus of claim 13, wherein the pre-defined element set is a pre-defined vocabulary, and
wherein the report generating circuitry is configured to:
calculate a conditional probability value of each semantic element in the pre-defined vocabulary using (i) words selected in previous time steps from among the plurality of time steps, and (ii) the identified plurality of the semantic representations using the third ML module; and
select the semantic element according to the conditional probability value of each semantic element in the vocabulary.

15. The apparatus of claim 11, further comprising:
training circuitry configured to:
determine parameters of the first ML processor using annotations of volume structures in the annotated 3D images;
determine parameters of the third ML processor using the annotated 3D images, the reports, and results generated from processing the annotated 3D images by the first ML processor and the second ML module; and
adjust the determined parameters of the first ML processor using feedback generated by the third ML processor while determining the parameters of the third ML module.

16. The apparatus of claim 11, further comprising:
training circuitry configured to:
determine parameters of one of the first ML processor and the second ML processor by training one of the first ML processor and the second ML processor using annotations of volume structures in the annotated 3D images; and
initialize the other one of the first ML processor and the second ML processor using the determined parameters.

17. The apparatus of claim 11, further comprising:
data obtaining circuitry configured to:
obtain history examination records generated by an image processing workstation, the history examination records including history 3D images, marks on the history 3D images generated in the image processing workstation, and history analysis reports associated with the history 3D images;
provide the history 3D images as the annotated 3D images;
provide the marks as annotations of the annotated 3D images; and
provide the history analysis reports as the reports associated with the annotated 3D images.

18. A non-transitory computer readable medium having instructions stored thereon that, when executed by one or more processors of a report generator, cause the report generator to:
identify a plurality of volume features in a 3D image using a first machine learning (ML) processor that is trained with annotated 3D images;
identify a plurality of semantic representations associated with the 3D image using a second ML processor that is trained with the annotated 3D images and reports associated with the annotated 3D images; and
generate a report of the 3D image based on the identified volume features and the identified plurality of semantic representations using a third ML processor that is trained with the annotated 3D images, the reports associated with the annotated 3D images, and outputs generated by the first ML processor and the second ML processor using the annotated 3D images and the reports associated with the annotated 3D images.

* * * * *